United States Patent
Giesen et al.

(10) Patent No.: US 8,133,696 B2
(45) Date of Patent: Mar. 13, 2012

(54) METHOD FOR DETERMINING THROMBIN ACTIVITY

(75) Inventors: Peter L. A. Giesen, Maastricht (NL); Timothy C. P. Van Asten, Maastricht (NL)

(73) Assignee: Thrombinoscope B.V., Maastricht (NL)

( * ) Notice: Subject to any disclaimer, the term of this patent is extended or adjusted under 35 U.S.C. 154(b) by 0 days.

(21) Appl. No.: 11/814,882

(22) PCT Filed: Jun. 6, 2007

(86) PCT No.: PCT/EP2007/005044
§ 371 (c)(1),
(2), (4) Date: Oct. 15, 2010

(87) PCT Pub. No.: WO2007/141023
PCT Pub. Date: Dec. 13, 2007

(65) Prior Publication Data
US 2011/0020850 A1    Jan. 27, 2011

(30) Foreign Application Priority Data
Jun. 6, 2006 (EP) ..................... 06011678

(51) Int. Cl.
*C12Q 1/56* (2006.01)
(52) U.S. Cl. .............. 435/13; 436/69; 600/369
(58) Field of Classification Search ............ 435/13; 436/69; 600/369
See application file for complete search history.

(56) References Cited

U.S. PATENT DOCUMENTS

| | | |
|---|---|---|
| 2006/0051828 A1 * | 3/2006 | Giesen et al. ............ 435/13 |
| 2009/0311730 A1 * | 12/2009 | Hemker et al. ............ 435/13 |
| 2010/0129841 A1 * | 5/2010 | Lassen et al. ............ 435/13 |

FOREIGN PATENT DOCUMENTS

WO    WO 03/093831 A1    10/2003

OTHER PUBLICATIONS

EPO 07785810.08 Written Opinion dated Jan. 4, 2011.

\* cited by examiner

*Primary Examiner* — Ralph Gitomer
(74) *Attorney, Agent, or Firm* — Kalow & Springut LLP; Scott D. Locke, Esq.

(57) ABSTRACT

Methods and kits to determine thrombin activity are provided. They have the great advantage that there is no need to measure the whole calibrator curve in each individual medium, since a single-point measurement is adequate.

16 Claims, 9 Drawing Sheets

METHOD FOR DETERMINING THROMBIN ACTIVITY

FIELD OF THE INVENTION

The present invention is in the field of diagnostics and relates in particular to a new method of determining biologically active forms of proteolytic enzymes, such as thrombin, in blood and other fluids, and to a test kit for carrying out this method.

BACKGROUND

Many laboratories in the fields of biochemistry, chemistry, medicine, diagnostics and the like are interested in the measurement of generation of enzymes in biological media. To this end, signal substrates are generally used that release a chromophore or fluorophore and, thus, after conversion will yield a chromogenic or fluorogenic signal that can be followed in time and measured.

A convenient method to follow the formation of enzyme in time in a biological medium is to add the substrate directly into the biological medium, e.g. the addition of a fluorogenic substrate to clotting plasma in which thrombin is formed. This has the advantage that the enzyme generation is measured in its physiological medium.

Drawbacks of this method are that the activity of the enzyme towards any physiological substrate that may also be present in this medium will compete with the signal substrate that is added and that the substrate may be completely consumed before the enzyme generation has finished. To minimize these effects, substrates are usually selected that do not bind to the enzyme too tightly (i.e. having a low $K_M$) and that are not converted too fast (i.e. having a low $k_{cat}$).

Another problem is that the measured signal is usually dependent on the turbidity and the color of the medium in which the reaction takes place. The same amount of enzyme in media from different sources or donors may thus yield a different amount of signal. Also the chromophore or fluorophore concentration may not be directly proportional to the amount of signal. This makes it more difficult to calculate the amount of enzyme present during the time course of the reaction. In order to accurately quantify the concentration of enzyme in time, all these effects have to be taken into account.

WO 03/093831 discloses a method for determining in real time the course of proteolytic activity, in particular thrombin activity, in a sample of blood or plasma as it appears in and disappears from the sample which comprises adding a thrombin substrate to the sample that, per unit time, produces a detectable signal in a quantity that bears relation to the amount of thrombin present. Simultaneously, in a control sample of the same blood or plasma in which thrombin generation is not triggered, the activity of a standard preparation with invariable thrombin activity is measured. The exact molar amount of thrombin present at any moment is obtained by comparison of the activity measured in clotting blood with a calibrator curve obtained from the simultaneously measured calibrator. It is also disclosed that if the color of the medium does influence the signal, then this calibrator curve can best be determined in each color of medium that is used.

The method of measuring the same amount of calibrated enzyme in another medium of different color or turbidity will produce a very similar calibration curve except for so-called medium-dependent effects.

This invention provides an alternative method in which this calibration curve is measured only once in one medium and the measurements in similar media of different color or turbidity are no longer performed by measuring the whole curve but can be replaced by a "single-point" measurement.

SUMMARY OF THE INVENTION

In accordance with the present invention a method is provided for determining the course of thrombin in time in clotting plasma which comprises the following steps:

a) adding a signal substrate to a reaction mixture that contains a predetermined amount of thrombin activity, said signal substrate causing a detectable signal related to the conversion product formed upon reaction with said thrombin activity;

b) determining the characteristics of the curve of signal in time in step a) by a mathematical procedure such that the initial slope of the curve is calculated and an estimate is made of its curvature;

c) adding a signal substrate to the plasma in which thrombin generation takes place, said signal substrate causing a detectable signal related to the conversion product formed upon reaction with thrombin;

d) adding a fluorescent compound to the same sample, or another sample of the same plasma as in which thrombin generation takes place, providing a detectable signal to be used as a measure for the influence of turbidity and/or color caused by the plasma on the signal;

e) comparing the measurement in step d) with the measurement in step a) to establish a relationship to correct for turbidity and color of the plasma in which thrombin generation takes place; and f) using the curvature of the measurement of 1) as determined in step b) to correct for non-linearities of the system in which the signal is measured and use the initial slope derived from step b) to calculate the concentration of thrombin in time from the signal measured in step c).

The invention further provides a kit for carrying out the method of claim 1, which comprises the following components:

- a known concentration of the enzyme that is measured or of a compound that has similar enzymatic activity toward the signal substrate as the enzyme that is measured.
- a trigger reagent to start the enzyme generation.
- an additive facilitating the diagnostic value of the test.
- a plasma that can be used for standardization and/or control.
- a reagent containing a signal substrate or a signal substrate to which the signal-producing leaving group is added.
- a software program directly loadable into the memory of a computer for calculating the enzyme activity as determined by a method disclosed herein, when said program is run an a computer.
- an instruction manual
- a calibrated amount of fluorophore to be used inside or outside the medium in which enzyme generation takes place
- a fluorescent source that can be used inside or outside the medium in which enzyme generation takes place.

The first biological sample is usually selected from blood, plasma which includes platelet-rich, platelet-poor or platelet-free plasma, saliva, serum, urine, cerebro-spinal fluid, sperm, and faeces.

When carrying out the method of the invention on blood samples, blood is usually collected in tubes that contain either sodium citrate or EDTA, or the like, so that free calcium ions in the blood are bound and thrombin formation and clotting is prevented. Hence, in order to start thrombin generation, calcium should be added shortly before the start of the measurement. However, in case blood is not collected in sodium citrate, or the like, this addition of calcium may not be necessary. For instance when the method is used in a way that makes it possible to start the experiment within minutes after blood taking.

The proteolytic activity to be determined is usually selected from the group of activated clotting factor activity, including thrombin, activated fibrinolytic factor activity, and activated component of the complement system activity. The determination of the course of thrombin activity, in real time, from a sample of blood or plasma according to the method of the present invention is a preferred embodiment.

The signal substrate which is used in the present method is preferably selected from the group of compounds comprising a leaving group, said leaving group giving a detectable conversion product upon reaction by the proteolytic enzyme formed. This conversion product is usually determined by spectroscopy, in particular fluorescence (preferred), optical density, and NMR. Accordingly, said leaving group normally is a fluorescent group, a chromophoric group, a group releasing hydrogen ions, or the like. A suitable and preferred signal substrate for carrying out the method of the present invention is Z-Gly-Gly-Arg-AMC. In addition, suitable detectable conversion products include p-nitroanilide and 7-amino-4-methyl-coumarin.

Suitable means with a constant known stable proteolytic activity for carrying out the method of the present invention, as defined above, include $\alpha_2$-macroglobulin-thrombin complex (preferred), staphylocoagulase-prothrombin complex, and gamma thrombin. In addition, any proteolytic enzyme can be used which is modified in its secondary recognition sites in that its active center remains intact but its functional interaction with proteins in the reaction mixture is abolished.

Useful protease activators for carrying out the present method include calcium ions, phospholipids, Tissue Factor, soluble Tissue factor, thromboplastin, kaolin, and elagic acid.

According to another aspect of the present invention said first biological sample further comprises a pharmaceutical agent to be tested for its influence on the proteolytic system under study, such as the haemostatic-thrombotic system. Suitable pharmaceutical agents which can be tested in the present method are antithrombotic agents, such as anti-platelet agents and anticoagulating agents, for example heparin, dermatan sulphate, a direct thrombin-inhibitor, for example hirudin, argatroban or melagatran, and a factor Xa inhibitor, for example thick anticoagulant protein.

These and other objects of the present invention will be explained below in more detail.

DEFINITIONS

Figure 1:
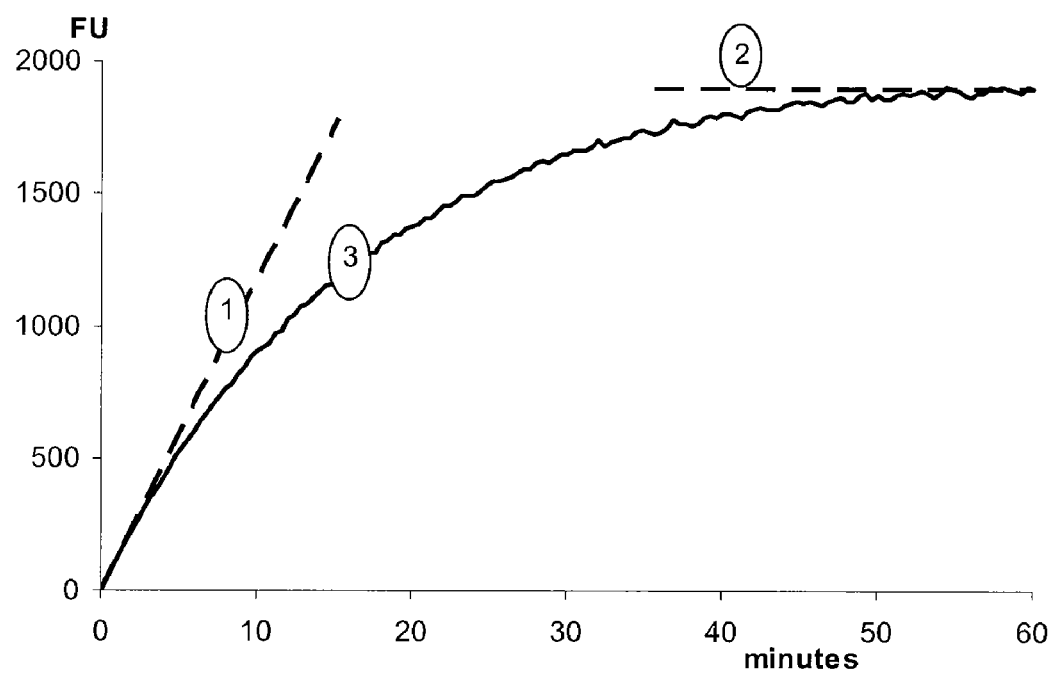
FIG. 1 illustrates a signal in time from a reaction mixture containing thrombin and a signal substrate.

The term "transiently active" as used herein in connection with proteolytic enzymes occurring in a blood or plasma sample refers to the fact that the enzymatic activity, once the physiological process is started with the means known to the art, first arises and then subsides again to (near) zero activity in the end.

The term "biological medium" as used herein, also referred to as "medium" as the case may be, refers to plasma, plasma with blood cells or whole blood or any other fluid of bodily origin or other, in which the biological process of enzyme activation and inactivation takes place.

The term "single point measurement" (SPM) refers to a technique in which a signal is measured during a short period of time as opposed to a series of measurements in which a change in signal over time is followed. An SPM can be repeatedly measured and then averaged, or can be measured only once.

As used herein, the term "signal substrate" means a substrate that is cleaved by proteolytic enzyme(s) present in the medium, from which a leaving group is split off which is detectable by optical, NMR or other methods. Leaving groups which are optical detectable are, for example, p-nitroanilide and 7-amido-4-methyl-coumarin. p-Nitroanilide absorbs at 405 nm and 7-amido-4-methyl-coumarin is fluorescent (excitation at 350 nm and emission at 460 nm). Examples of NMR-active leaving groups are those containing $^{31}P$, $^{13}C$, or any other atom which can be detected with NMR or a similar technique. Also $H^+$ ions can be used as leaving group, which can be detected by measuring changes in the pH. Also amperometric substrates can be used in which the enzyme of which the concentration is followed in time is responsible for a change of an added substrate to the reaction mixture which can be followed by measuring electrical conductivity.

DETAILED DESCRIPTION OF THE INVENTION

As mentioned hereinbefore, an established way to determine enzyme formation in a sample of biological medium is to add a signal substrate that is specific for that enzyme to the medium and to follow the signal in time. This signal not only depends on the changing concentration of enzyme but also on various medium-dependent and medium-independent parameters. Medium-dependent parameters include turbidity and absorption spectrum (e.g. color) of said medium. Medium-independent parameters include concentration of enzyme, concentration of substrate, enzyme kinetic parameters of the signal substrate towards the enzyme (such as $K_m$ and $k_{cat}$), technique of measurement, materials in which the medium resides during measurement, volumes that are used, and the like.

WO 03/093831 discloses that in order to correct for these effects, a calibrated amount of enzyme is added to the medium. Addition of signal substrate will then result in a signal in which medium dependent as well as medium-independent influences are seen. This measurement is then used to calculate the unknown amount of enzyme that is formed in (another sample of) the biological medium. That is, this curve serves as a "calibrator curve" that contains all information necessary to translate the signal into a concentration of enzyme in time that is formed during the biological reaction in another sample of the same medium. In this setup, it is necessary that the calibration curve is measured in a medium with the same color and turbidity as in which enzyme formation takes place. This is the most optimal way to correct for the medium-dependent influences on the signal.

The present invention provides a reliable, fast and convenient method to determine the change in concentration of enzyme in time in a biological medium in the presence of a signal substrate, wherein appropriate corrections are made for substrate consumption, color-dependency of the signal and non-linearity between the concentration of the chromophore or fluorophore and the amount of signal. The signal that is measured will be corrected for effects that are different for each sample (sample-dependent variability) and effects that are the same for all samples that are measured under similar conditions. Such variabilities include effects of substrate consumption, inner-filter effect, instrument specific effects, experimental setup dependent effects and more. The key of this invention is to measure the sample-independent variability separately from the sample-dependent variability. The sample-dependent variability can then be measured in a more convenient and more facile way.

This single-point measurement consists of a measurement of some signal-producing source of which the signal travels through the medium such that the amount of signal is a measure for the color and/or turbidity of the medium. The method comprises essentially the measurement of a calibrator curve in a suitable medium, such as a buffer, to determine the characteristics of the measured curve. These characteristics describe the sample-independent variability and will then allow to obtain this whole curve or a sufficient part of the curve again through a mathematical procedure based on a single-point measurement of sample dependent variability in a sample of a medium in which the enzyme generation takes place. This has the great advantage that there is no need to measure the whole calibrator curve in each individual sample of medium but that a single-point measurement is adequate. This single point measurement should be a measure for the variability of signal caused by the medium itself. It could comprise of the measurement of a fixed concentration of fluorophore in the biological medium of which the result is a measure for the donor-to-donor differences in color of plasma.

Thrombin appears and disappears in plasma during coagulation. When a suitable fluorogenic substrate is added to this reaction, fluorescence can be followed in time and from this fluorescence the concentration of thrombin can be calculated. However, the signal that is measured suffers from non-linearities of the system due to substrate consumption and the non-linear relationship between amount of fluorophore that is produced and the amount of fluorescence. This is illustrated in FIG. 1 where a fixed amount of thrombin in buffer is measured in a fluorometer in the presence of the fluorogenic substrate Z-Gly-Gly-Arg-AMC which clearly shows a curve that bends off. Typically such a curve has three characteristics: its initial slope (1), its end-level (2) and its curvature (3).

Initial Slope (1)

The initial slope is dependent, among others, on the color of the medium in which the reaction is followed, on substrate concentration and on thrombin concentration. By definition, the initial slope does not suffer from the effects of substrate consumption and inner filter effect because at time zero no substrate is consumed and no fluorophore is formed. Therefore the initial slope gives the translation between Fluorescent Units (FU) per minute and concentration of enzyme: FU/min×C=[thrombin]. This C can only be used to calculate thrombin in time in a sample in which thrombin generation takes place when the signal is corrected such that during the whole reaction C stays at a fixed value.

End-Level (2)

When the plateau is reached then the substrate is completely consumed and/or the system has reached its limit of fluorescence, i.e., more fluorophore does not result in more signal.

The measured amount of fluorescence at the end level thus depends on fluorophore concentration and the limit of the system. Also this end level depends on the color of the medium in which fluorescence is measured.

Curvature (3)

Figure 2:
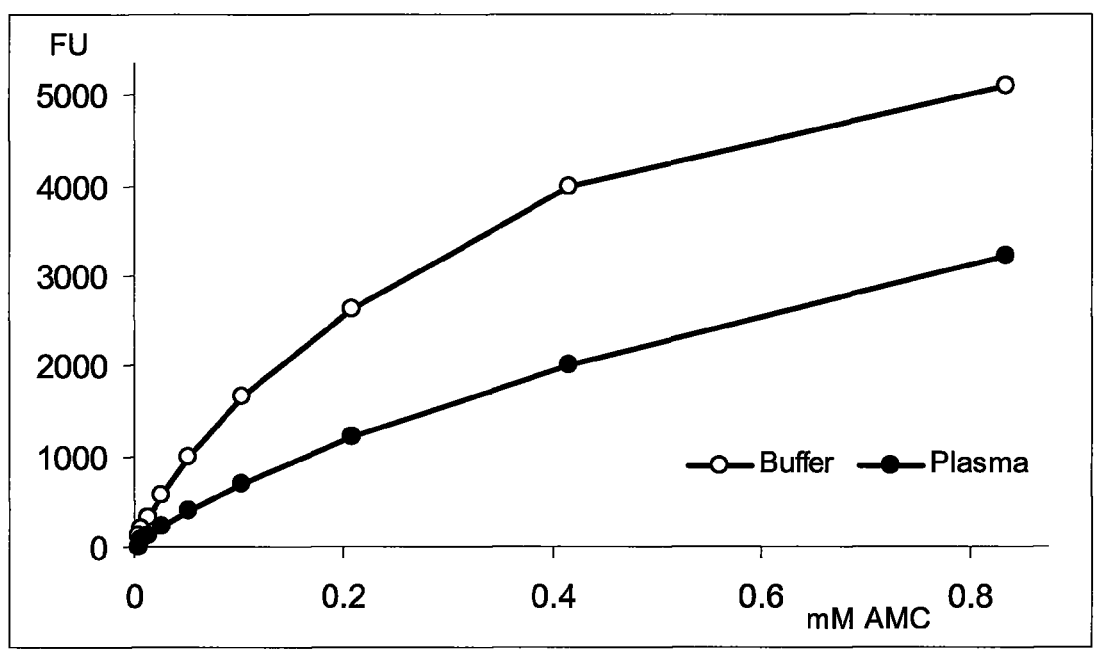
FIG. 2 illustrates a fluorophore (amino methyl coumarin, AMC) concentration range in buffer and plasma. Due to inner filter effect (IFE) the curve bends off. It can also be seen that the amount of signal at equal fluorophore concentrations is substantially different for the two different media.
Figure 3:
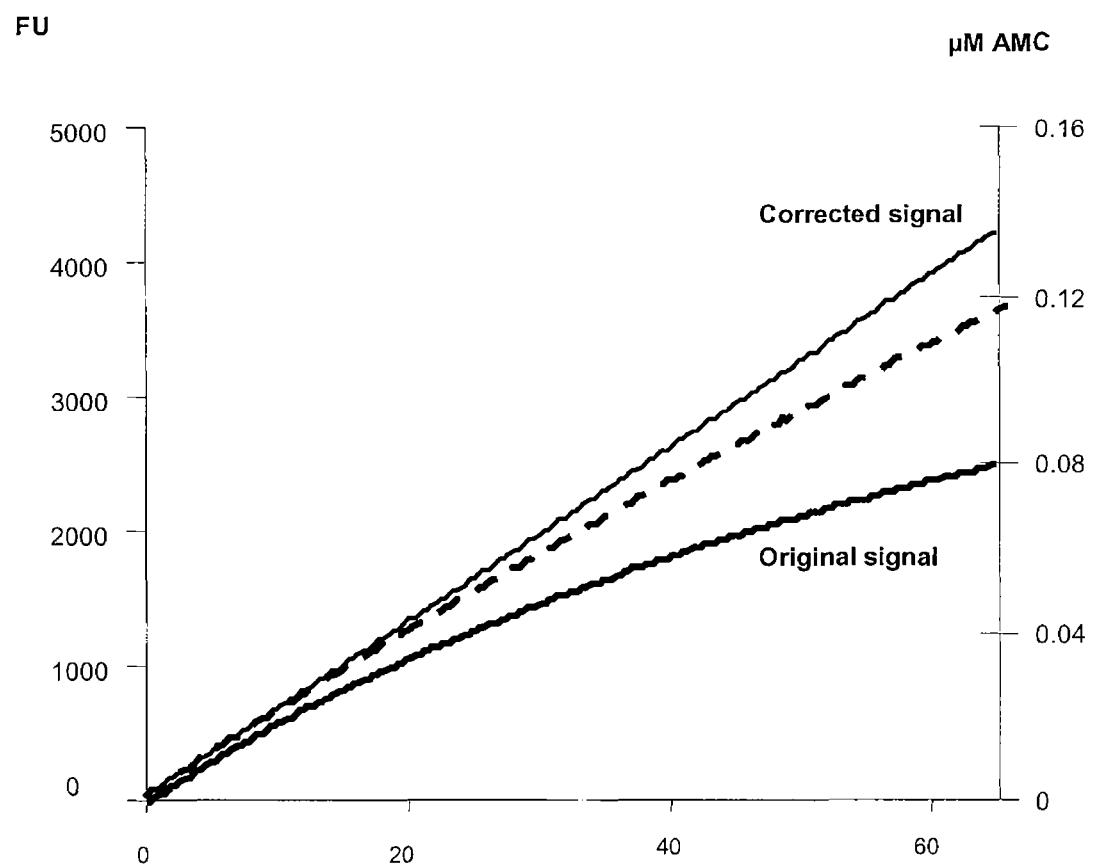
FIG. 3 shows a) a calibrator curve (bended line, black), b) the same curve which has been corrected for IFE (dashed) and c) the same curve which has been corrected for IFE and then also for substrate consumption (straight line). The original curve is plotted according to the values of the left-hand axis (fluorescent units, FU). The dashed curve is calculated from the relationship between fluorescence and AMC concentrations as shown in FIG. 2.

The curvature is dependent on non-linearity between amount of fluorophore and amount of fluorescent signal as well as substrate consumption. The relationship between the concentration of fluorophore and amount of measured fluorescence is often not linear, it is caused by the fact that increasing fluorophore concentrations give relatively less fluorescence (inner filter effect). A second effect is the conversion of the substrate which leads to a lowering of the substrate concentration (see FIGS. 2 and 3). When these substrate concentrations are below or near the Km of the substrate then the velocity by which thrombin converts the substrate will go down with the lowering of substrate. Depending on the choice of substrate, the measured enzyme and the measurement system the curvature can be strong or absent.

Figure 4:
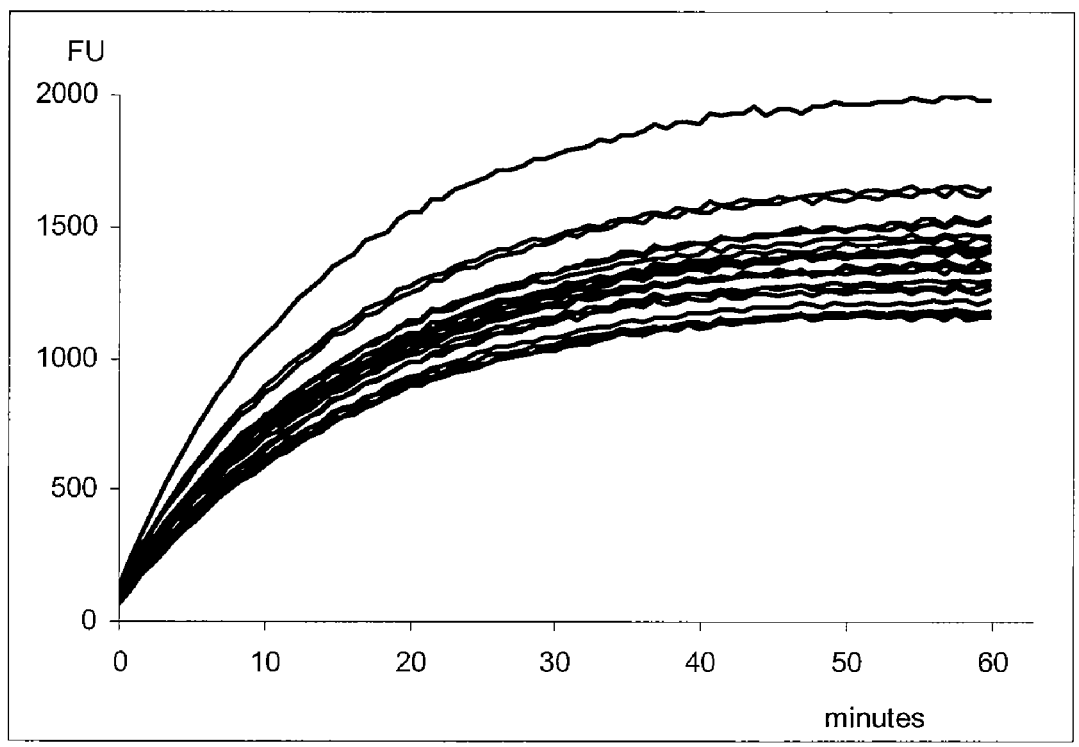
FIG. 4 shows the curves from the measurements of the same concentration of thrombin activity in different plasmas.

FIG. 4 shows an example of a measurement of the same concentration of thrombin activity (derived from alpha2-Macroglobulin-thrombin complex (α2M-IIa) measured in plasma from different donors). It is obvious from this figure that 1) the same enzymatic activity in these different plasmas show large variations and that 2) all curves bend off towards a plateau. These curves contain all information necessary to correct for the donor-to-donor differences in color of plasma as well as the non-linearities of the system. The curves of FIG. 4 can be mathematically fit according to the formula:

$$FU(t)=FU(0)+MAX*(1-EXP(time*K)),$$

wherein
FU(t) is fluorescence in time,
FU(0) is the initial fluorescence value,
MAX is the end level, and
K describes the curvature.

Although this logarithmic formula usually gives a good approximate fit, alternative mathematical formula's can be used such as a polynomial function, a hyperbola or combinations of these, or other alternatives. The formula that is used is not crucial, it is just needed to be able to describe the curve such that corrections can be made for curvature and color differences of the media that are used.

Figure 5:
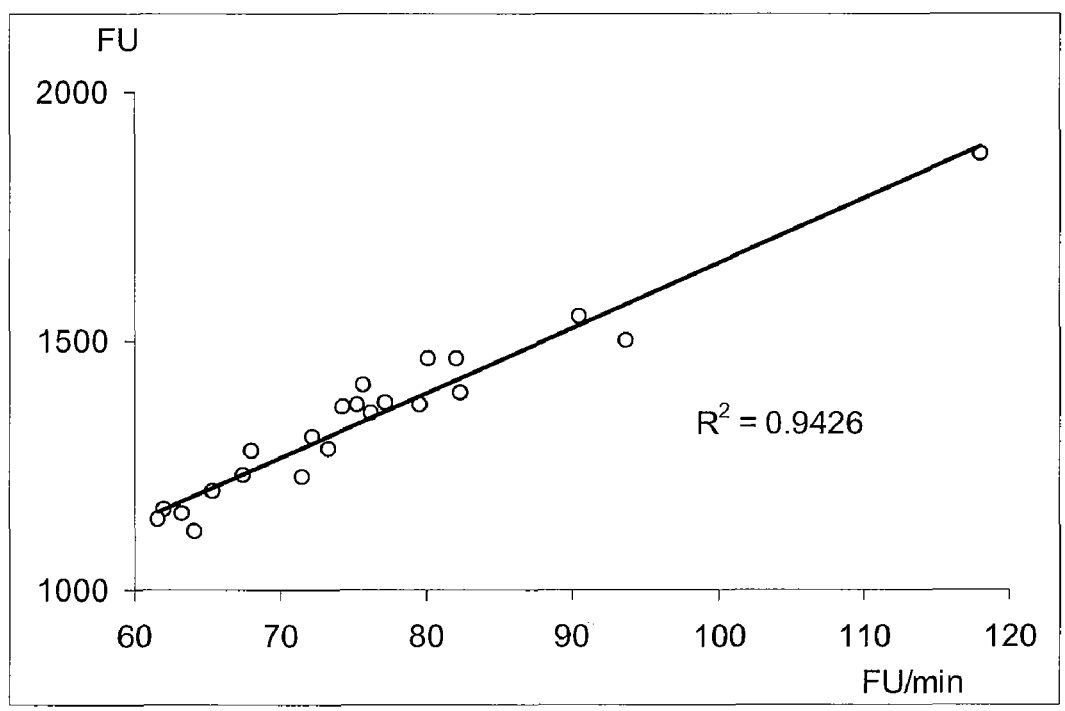
FIG. 5 shows the relationship between the initial slope of the curves and their end levels.

FIG. 5 shows surprisingly an excellent relationship between the initial slope of each curve and its end level. Once this relationship has been established the initial slope can be calculated from the end level values only. The curvature, described by parameter K, is identical for all curves and is not influenced by the color of the medium. Therefore K, that is influenced by the artifacts of the system such as substrate consumption and inner filter effect, needs only to be measured once. After that, the curves can be generated by the measurement of the end level only. This end level is measured in the situation in which all substrate is converted into fluorophore. Addition of this amount of fluorophore to each individual plasma, instead of addition of a combination of fluorogenic substrate with enzyme, would also result in the same amount of signal. This means that once K is known and the end-level is known from a single point measurement of fluorophore addition only, the whole curve can be generated for each individual plasma, as if all these curves were measured in all these individual plasmas.

Once K is known and the end level is measured, the values of the conversion of the signal substrate that is derived from the enzyme generation curves, can be corrected. This invention proposes to use only a single-point measurement, determined in each individual plasma, in order to correct for the influence of the color of the medium. This single-point measurement can also be used to correct the curves for non-linearities. Although the end level measurement is probably the most accurate parameter to correct for the non-linearities of the system, any value within the curve can be used to describe the whole curve. For instance if the value of the signal of the curve is known that gives 50% of the end level then an appropriate mathematical formula will be able to extra- and inter-polate the remaining curve. The closer the value is to the end level the more accurate the fit will become. Single-point measurements in the case of calibrator curves that do not bend off towards a plateau or in case non-linearities of the system are not considered to be important can still be used for correction of color only. In the latter case the value of parameter K is not used.

The measurement of thrombin generation in plasma is an excellent tool to assess the functionality of the thrombotic-hemostatic system. As mentioned above, WO 03/093831 discloses a method of measuring thrombin generation in clotting plasma. This method is now widely used and involves in the current practice fluorometric detection. Plasma is divided into two samples, in one sample thrombin generation is triggered (TG-sample) and to the other sample a calibrated amount of α2M-IIa activity is added. Both samples receive the same amount of fluorogenic substrate and fluorescence is followed in a fluorometer. The calibrator curve (similar to FIG. 1) bends off due to inner filter effect and substrate consumption. From this calibrator curve, the amount of thrombin in time that is formed in the TG sample can be calculated:

a) the parameters that are needed to "straighten up" the calibrator curve, can be used to make the corrections for the fluorescence signal derived from the TG-sample. See FIG. 8A below. The accuracy of this correction increases with longer measurements of the calibrator curve, that is, the closer the measurement approaches the end level of the curve, the more accurate the mathematical parameters needed for correction can be estimated. This means that a minimum amount of time is needed for the measurement of the curve, in actual practice usually at least 20 minutes. Software commercially available from Thrombinoscope BV, The Netherlands (www.thrombinoscope.com) calculates for each amount of fluorescence in the TG curve a corrected value of fluorescence. The measured values of fluorescence in the TG-sample are then replaced by corrected values.

b) from the calibrator curve a conversion curve can be derived by which the first derivative of the fluorescence in time of the TG sample, FU/min (fluorescent units per minute) can be multiplied to reach the concentration of thrombin because the calibrator curve was measured with a known amount of thrombin activity.

It should be realized that the parameters under a) are in fact not dependent on the color or turbidity of the medium. But because the signal changes with the color of the medium, WO 03/093831 teaches that in the method disclosed the calibrator curve should be measured in (another sample of) the same plasma as in which thrombin generation takes place (the TG sample). Since the signal is remarkably different between donors due to the variations in plasma-color, the calibrator curve needs to be measured in each individual plasma. The conversion factor mentioned under b) is dependent on the color of the plasma in which fluorescence is measured.

The present invention provides an improvement to the thrombin generation test disclosed in WO 03/09831 by allowing correction for plasma color and turbidity.

Figure 6:
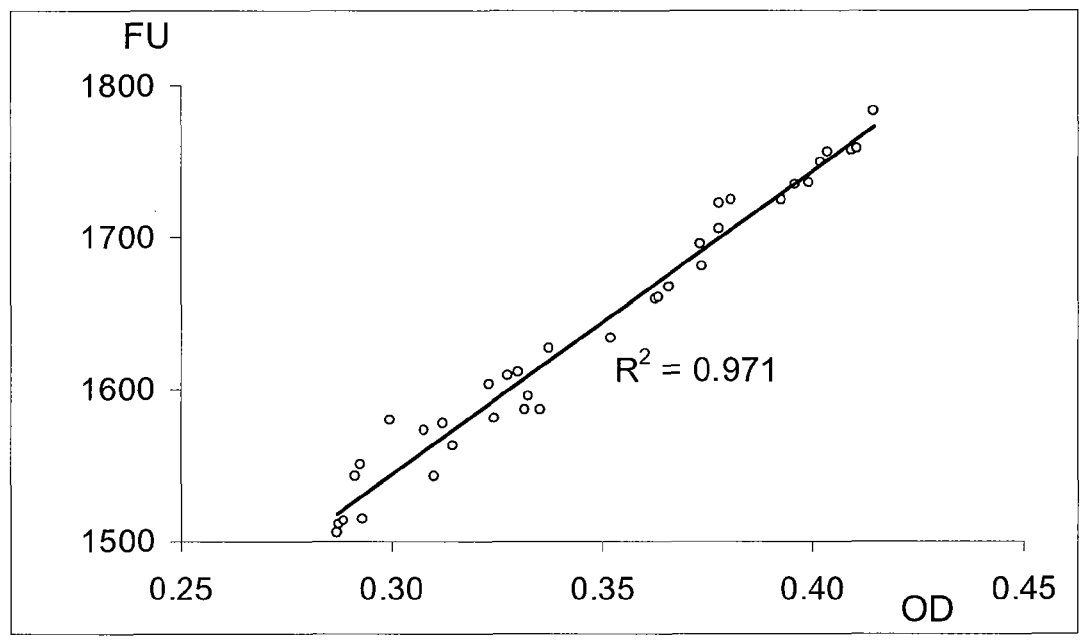
FIG. 6 shows the relationship between the optical density of plasmas of different donors and the end level of the calibrator curve measured in the same plasmas.

According to this invention only one measurement in the plasma sample is needed to obtain sufficient information to correct for color variations and/or inner filter effect and substrate consumption in the sample. In the fluorometer that is employed one measurement in any suitable medium is needed to establish the characteristics of the calibrator curve. Once these are known, only a single point measurement needs to be performed for each color of medium. This single-point measurement can be done in various ways, for example:

2. Measurement of the optical density of the media. There is a good relationship between the variations in optical density, measured at the appropriate wavelength, between different plasmas and the different end levels or initial slopes of the calibrator curves (FIG. 6). An OD measurement only takes a few seconds or less and once this relationship is established the correction can be made.

3. Fluorophore can be added to the plasma, the amount of fluorescence that is measured will depend on the color of the plasma. The amount of fluorescence gives an excellent measure for the end level or initial slopes of the calibrator curve. When the concentration of fluorophore equals the amount of substrate then the measured value will equal the end level. Lower concentrations of fluorophore will also be adequate as long as the relationship between this single-point measurement and the variability of fluorescence due to the color of the different media is established. Even at zero concentration of fluorophore, that is, fluorescence is measured of plasma only, the measured value depends on the color of the plasma. However, addition of fluorophore greatly increases accuracy of the correction. A convenient way to add fluorophore to each plasma is the addition of fluorophore to the fluorogenic substrate itself. For instance if a concentration of fluorophore is added that equals 5% of the concentration of the substrate initial substrate concentration then the measurement will show a certain offset of fluorescence at zero time. This offset will be an excellent measure of how the signal is influenced by color and turbidity of the sample and can be used to correct for these effects. This would have the great advantage that the very same sample of plasma in which thrombin generation takes place can also be used for calibration. This would reduce the minimal amount of sample necessary to do the test and would increase the measurement throughput.

Figure 7:
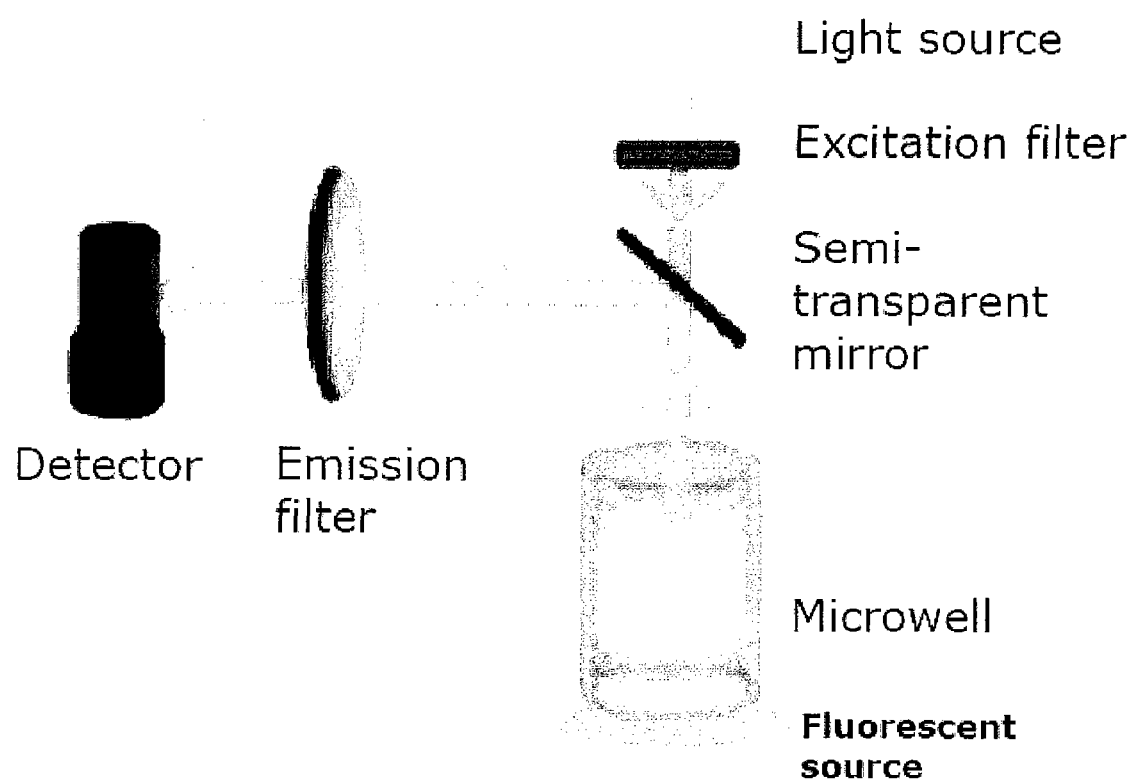
FIG. 7 shows a drawing of a possible setup in which the single point measurement is determined from a fluorescent source that is placed underneath a microtiter well.

4. A fluorescence source can be positioned such that the excitation light has to pass through the sample to reach the source and/or the emission light has to pass through the sample to reach the detector. For example, a transparent cuvette filled with plasma can be placed next to a cuvette filled with fluorophore. When the emission light first passes the sample and then hits the fluorophore-solution then the measurement will be proportional to the variations of sample colors. Instead of the fluorophore solution, other fluorescent sources may be used such as dry fluorescent fluorophore bound to a suitable material or a mesh or gel or maze or absorbing material that is made fluorescent to which the plasma, platelet-rich plasma or whole blood is added. A possible setup using a microtiter plate is shown in FIG. 7. In this example, the fluorescent source is placed outside and underneath the microtiter well.

The invention further provides a kit for carrying out the method of the present invention as disclosed hereinbefore. Such a kit conveniently comprises one or more of the following components in suitable containers or other conventional packaging means:

- a known concentration of the enzyme that is measured or of a compound that has similar enzymatic activity toward the signal substrate as the enzyme that is measured.
- a trigger reagent to start the enzyme generation. In particular, when such a trigger is used to measure thrombin activity in whole blood, or platelet-rich or platelet-poor or platelet-free plasma, then suitable triggers are reagents that contain one or more of the following compounds: purified or recombinant tissue factor, phospholipid vesicles, microparticles, clotting factors, collagen, platelet activators, thrombin.
- an additive facilitating the diagnostic value of the test. In particular, when such an additive is used to measure thrombin activity in whole blood, or platelet-rich or platelet-poor or platelet-free plasma, then suitable additives are purified or synthesized (recombinant) thrombomodulin, activated protein C, antithrombotic drugs, antiplatelet drugs, purified or synthesized (recombinant) clotting factors
- a plasma that can be used for standardization and/or control.
- a reagent containing a signal substrate or a signal substrate to which the signal-producing leaving group is added.
- a software program directly loadable into the memory of a computer for calculating the enzyme activity as determined by a method disclosed herein, when said program is run an a computer.
- an instruction manual
- a calibrated amount of fluorophore to be used inside or outside the medium in which enzyme generation takes place
- a fluorescent source that can be used inside or outside the medium in which enzyme generation takes place. This can be a liquid, a gel, an absorbant material, a maze or any form of material that is fluorescent or that has been made fluorescent.
- a reagent containing any combination of compounds or additives mentioned above.
- disposables such as cuvettes, microtiter plates or other material that is necessary to conveniently execute the measurement.
- a dongle that is detected by the software program such that the software does not run without its presence. Such a dongle that can be inserted in the USB port of the computer on which the software runs serves as a copy-protection.

The kit may suitably comprise freeze-dried reagents.

The invention is further illustrated by the following example which, however, is not to be construed as limiting the scope of the invention in any respect.

EXAMPLE

Figure 8A:
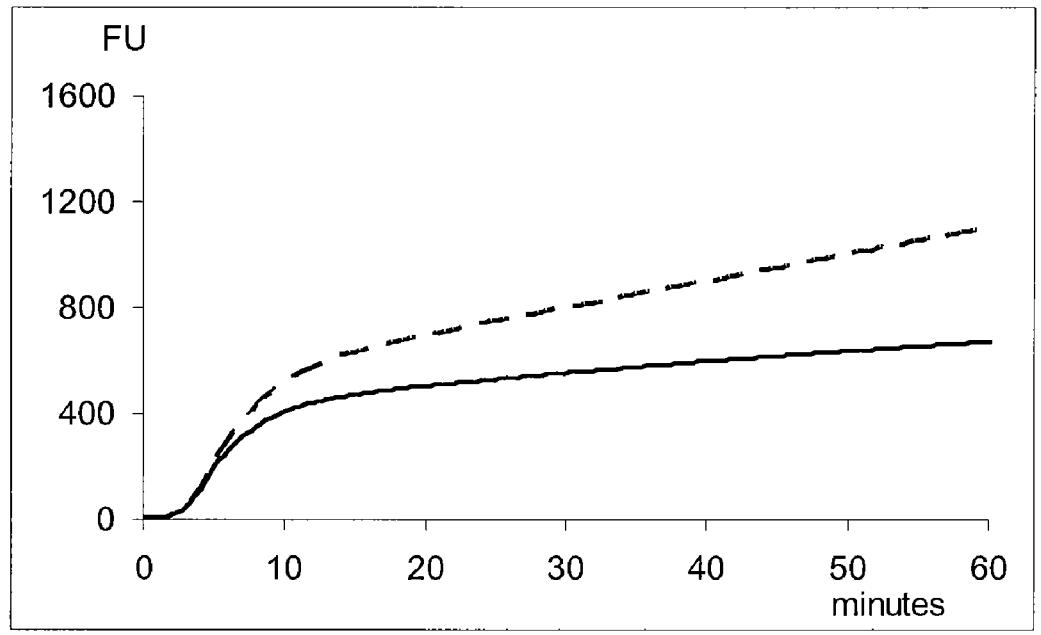
FIG. 8A shows the uncorrected and corrected fluorescent values of a measurement of thrombin generation in plasma.

FIG. 8A shows the uncorrected fluorescent signal measured from a reaction mixture containing $\frac{2}{3}^{rd}$ platelet poor plasma, 416 µM of the fluorogenic thrombin substrate Z-G-G-R-AMC, 4 µM of procoagulant phospholipid vesicles and 5 pM recombinant tissue factor. At time zero the reaction is started by the addition of the fluorogenic substrate and calcium to the citrated plasma. The dashed line shows the corrected signal for this reaction in which correction has been made for inner filter effect and substrate consumption.

Figure 8B:
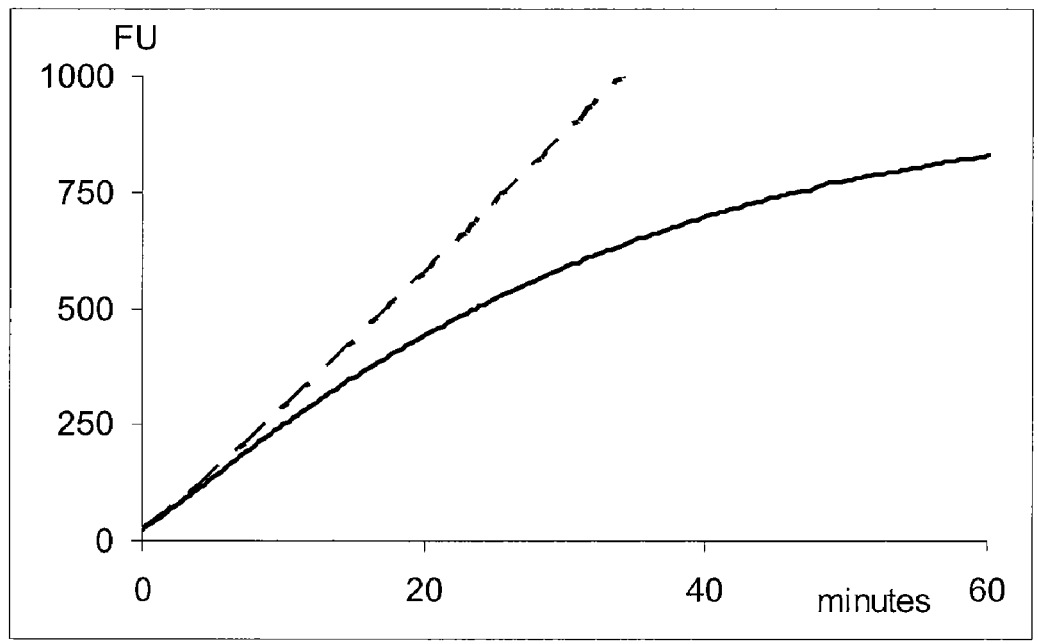
FIG. 8B shows a measurement of thrombin in buffer, the dashed line shows the correction of the signal for IFE and substrate consumption.

FIG. 8B shows a measurement of 100 nanomolar of thrombin in Hepes buffered saline pH 7.35. This calibrator curve is mathematically fit according to the formula $FU(t)=FU(0)+MAX*(1-\exp(K*t))$. A single point measurement of a concentration of fluorophore that equals the substrate concentration in another sample of the same plasma as in which thrombin generation takes place is used to correct the fluorescent signal in FIG. 8A using the formula:

$$FU\_corrected=-SPM*LN[FU(0)+SPM-FU]+SPM*LN(SPM)+FU(0)$$

wherein

SPM is the single point measurement of fluorescence,

FU(0) is the fluorescence at time zero of the reaction, and

FU is the uncorrected value of fluorescence.

Figure 9:
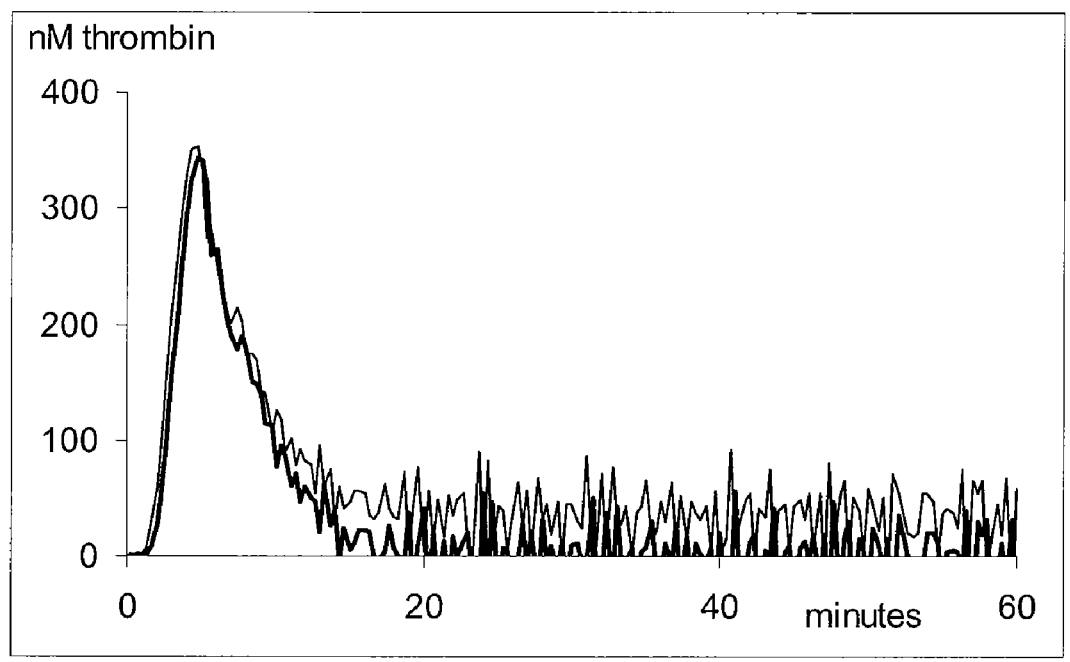
FIG. 9 shows the values, calculated according to the present invention, of thrombin in time before (thin line) and after (fat line) correction for the amidolytic activity of a2M-IIa.

Using this formula the calibrator curve will change into a straight line (8B, dashed line). This straight line closely approximates the initial slope of the curve. The first derivative of the corrected curve in FIG. 8A (FIG. 9) needs to be translated from FU per minute into nanomolar thrombin in time. To this end, the initial slope is calculated from the single point measurement SPM using the formula: initial slope=$-SPM*K$ in which K is calculated from the measurement in FIG. 8B. So in each medium only a single point measurement is needed to correct for non-linear behaviour of the fluorescent signal as well as for the translation between velocity of increase in fluorescence (FU/min) and concentration of thrombin. Finally the thrombin generation curve needs to be corrected for the proportion of substrate conversion not caused by thrombin but by the amidolytic activity of the α2M-IIa complex.

In this example, the calibrator curve was measured completely until the end level was reached, which means that the value of SPM in the formula equals the end level. However, it is not necessary to complete the measurement, the mathematical fit is able to make a reasonable approximation of the end level by extrapolation. Alternatively, all information necessary to make the correction can be gathered by measuring only the initial slope of the calibrator curve V(0), which just takes a few minutes to complete, and in addition perform a measurement of an amount of fluorophore that equals the substrate concentration in a reaction mixture that contains the same buffer as in which the calibrator curve was measured. This measurement will yield a value FU_max that immediately gives the amount of fluorescence at the end level of the calibrator curve. The parameter K described above equals $-V(0)/FU\_max$. In this manner K is measured within a few minutes. As explained before, this K is not dependent on the color differences of the media. Also here it is not necessary to measure a concentration of fluorophore that exactly matches the substrate concentration, the closer the concentration is to the substrate concentration the more accurate a description of the whole curve can be made.

The present invention offers a convenient test method to determine in real time the course of proteolytic activity in a sample of a biological medium, in particular thrombin activity in blood or plasma or platelet-rich plasma, which is corrected for medium-independent parameters but also for medium-dependent parameters, such as turbidity and color of the medium, thereby providing a reliable, elegant and simple way of measuring the proteolytic activity in samples by a single-point measurement in each sample and a calibrator curve measured only once in a suitable medium such as buffer.

This test method is useful e.g. for measuring the time course of thrombin activity in vitro, i.e. measuring active thrombin in a sample following its generation, or as it develops in a clotting sample of whole blood or plasma containing platelets or plasma without platelets. It is also useful for monitoring the condition of a patient, including the detection or monitoring of a pathological condition related to blood coagulation deficiency. It is further useful for the screening of substances, including for the screening of drugs who could interact with the coagulation process, especially with thrombin activity.

The present disclosure is to be considered as in all respects illustrative and not restrictive, the scope of the invention being indicated by the appended claims, and all changes within the meaning and range of equivalency are intended to be embraced therein.

The invention claimed is:

1. A method for determining the course of thrombin activity in time in a plasma sample, the method comprising the following steps:
   a) adding a signal substrate to a reaction mixture that contains a predetermined amount of thrombin activity, said signal substrate causing a detectable signal related to a conversion product formed upon reaction with said thrombin activity, and measuring the detectable signal;
   b) providing a curve showing the time course of signal development in the reaction mixture, and determining an initial slope of the curve, the curve's end-level and the curve's curvature;
   c) adding a signal substrate to a plasma sample in which thrombin generation takes place, said signal substrate causing a detectable signal related to a conversion product formed upon reaction with thrombin, and measuring the detectable signal to provide a curve showing an intensity of fluorescence in time;
   d1) adding a fluorescent compound to the same sample of step c), or another sample of the same plasma in which thrombin generation takes place, providing a detectable signal to be used as a measure for the influence of turbidity and/or color caused by the plasma on the detectable signal; or
   d2) measuring an optical density of the same sample in step c); or another sample of the same plasma in which thrombin generation takes place, providing a measure for the influence of turbidity and/or color caused by the plasma on the detectable signal; or
   d3) providing a fluorescent source and positioning the fluorescent source such that excitation light passes through the plasma sample to reach the fluorescent source and/or emission light passes through the sample to reach a detector, and measuring the detectable signal, providing a measure for the influence of turbidity and/or color caused by the plasma on the signal;
   e) comparing the measurement of detectable signal in any one of steps d1), d2) or d3) with the measurement of detectable signal in step a) to provide a correction factor for turbidity and color of the plasma in which thrombin generation takes place; and
   f) using the curvature of step b) to correct for non-linearities in the curve of step c), using the correction factor of step e) to correct the curve of step c) for turbidity and color of the plasma, and using the initial slope of step b) to calculate the concentration of thrombin in time from the curve of step c) to determine the course of thrombin activity.

2. The method according to claim 1, wherein prior to step c) the method further comprises adding a protease activator to said plasma sample to generate proteolytic activity.

3. The method of claim 1, wherein said plasma sample is selected from the group consisting of plasma, platelet-rich plasma, platelet-poor plasma or platelet-free plasma.

4. The method of claim 1, wherein the signal substrate is selected from the group consisting of compounds comprising a leaving group, said leaving group giving a detectable conversion product upon reaction by the thrombin activity formed.

5. The method of claim 4, wherein the signal substrate is the fluorogenic substrate Z-Gly-Gly-Arg-AMC.

6. The method of claim 1, wherein the detectable conversion product is determined by spectroscopy, fluorescence, optical density, NMR, or electrical conductivity.

7. The method of claim 4, wherein the leaving group is a fluorescent group, a chromophoric group or a group releasing hydrogen ions.

8. The method of claim 1, wherein the detectable conversion product is p-nitroanilide or 7-amino-4-methyl-coumarin.

9. The method of claim 2, wherein the protease activator is selected from the group consisting of calcium ions, phospholipids, Tissue Factor, soluble Tissue factor, thromboplastin, kaolin, and elagic acid.

10. The method of claim 1, wherein the plasma sample further comprises a pharmaceutical agent to be tested for its influence on a proteolytic system under study.

11. The method of claim 10, wherein the proteolytic system is a haemostatic-thrombotic system.

12. The method of claim 10, wherein the pharmaceutical agent is an antithrombotic agent, an anti-platelet agent or an anticoagulant agent.

13. The method of claim 12, wherein the antithrombotic agent is selected from the group consisting of heparin, dermatan sulphate, a direct thrombin-inhibitor, hirudin, argatroban or melagatran, a factor Xa inhibitor, and a thick anticoagulant protein.

14. The method of claim 1, wherein in step d3) the fluorescent source is a fluorophore solution or a dry fluorescent fluorophore bound to a material or a mesh or gel or absorbing material that is made fluorescent to which the plasma is added.

15. The method according to claim 1, wherein the initial slope, the curvature and its end-level in step b are determined by fitting the time course of signal development to the formula:

$$FU(t) = FU(0) + MAX*(1 - \exp(K*t)),$$

in which FU(t) is the fluorescence in time of the curve in step b, FU(0) is the fluorescence at the start of the measurement, MAX is the end-level and K is a constant, to yield MAX + FU(0) as the end level, K as a measure for the degree of curvature and $-MAX*K$ as the initial slope.

16. The method according to claim 1, wherein the correction for non-linearities in step f is made by taking the fluorescence values measured in step c and enter them into the formula:

$$FU\_corrected = -SPM*LN[FU(0)+SPM-FU] + SPM*LN(SPM)+FU(0)$$

in which FU_corrected is the fluorescent value after correction for non-linearities, as in step f, SPM is the single point measurement as a measure for the influence of turbidity and/or color caused by the plasma on the signal in step d; FU(0) is the fluorescence at time zero of the reaction measured in step c, and FU is the fluorescence value measured in step c.

* * * * *